United States Patent [19]
Schilling et al.

[11] Patent Number: 5,976,128
[45] Date of Patent: Nov. 2, 1999

[54] ELECTROSURGICAL HIGH FREQUENCY GENERATOR

[75] Inventors: Bertram Schilling, Mauenheim; Udo Trockweiler, Immendingen, both of Germany

[73] Assignee: Gebrueder Berchtold GmbH & Co., Tuttlingen, Germany

[21] Appl. No.: 08/874,758

[22] Filed: Jun. 13, 1997

[30] Foreign Application Priority Data

Jun. 14, 1996 [DE] Germany .......................... 196 23 840

[51] Int. Cl.⁶ ................................................ A61B 17/39
[52] U.S. Cl. ................................ 606/34; 606/35; 606/41
[58] Field of Search .............................. 606/33, 32, 34, 606/35, 37, 38; 607/99, 101, 11

[56] References Cited

U.S. PATENT DOCUMENTS

| | | |
|---|---|---|
| 3,601,126 | 8/1971 | Estes . |
| 4,126,137 | 11/1978 | Archibald . |
| 4,184,492 | 1/1980 | Meinke . |
| 4,474,179 | 10/1984 | Koch . |
| 4,658,819 | 4/1987 | Harris . |
| 4,848,335 | 7/1989 | Manes ..................... 128/303 |
| 4,969,885 | 11/1990 | Farin . |
| 5,087,257 | 2/1992 | Farin et al. ................. 606/35 |
| 5,372,596 | 12/1994 | Klicek et al. ............... 606/35 |
| 5,514,129 | 5/1996 | Smith . |
| 5,558,671 | 9/1996 | Yates ........................ 606/38 |
| 5,722,975 | 3/1998 | Edwards et al. ............. 606/34 |
| 5,772,659 | 6/1998 | Becker et al. .............. 606/34 |

FOREIGN PATENT DOCUMENTS

| | | |
|---|---|---|
| 0219568 | 10/1989 | European Pat. Off. . |
| 2502935 | 10/1982 | France . |
| 1139927 | 11/1962 | Germany . |
| 2803017 | 7/1978 | Germany . |
| 2710752 | 9/1978 | Germany . |
| 2504280 | 8/1980 | Germany . |
| 2535341 | 9/1980 | Germany . |
| 3120102A1 | 12/1982 | Germany . |
| 3239640C2 | 1/1987 | Germany . |
| 3120102C2 | 8/1987 | Germany . |
| 3510586C2 | 7/1988 | Germany . |
| 3830193A1 | 3/1990 | Germany . |
| 4205213A1 | 8/1993 | Germany . |
| 4217999A1 | 12/1993 | Germany . |
| 897961 | 6/1962 | United Kingdom . |
| WO 93/03677 | 3/1993 | WIPO . |

Primary Examiner—Linda C. M. Dvorak
Assistant Examiner—David M. Ruddy
Attorney, Agent, or Firm—Townsend and Townsend and Crew LLP

[57] ABSTRACT

An electrosurgical high frequency generator has a high frequency oscillator and, connected thereto, a regulatable power stage to which a patient current circuit with active and neutral electrodes can be connected via an output transformer. Three parameter sensors for the high frequency current, the high frequency voltage and the arc formation are provided at the output circuit and are connected via an interface to a microcomputer which in turn controls the power stage. In accordance with the invention, a tissue impedance sensor is additionally provided which is likewise connected to the microcomputer via the interface.

12 Claims, 1 Drawing Sheet

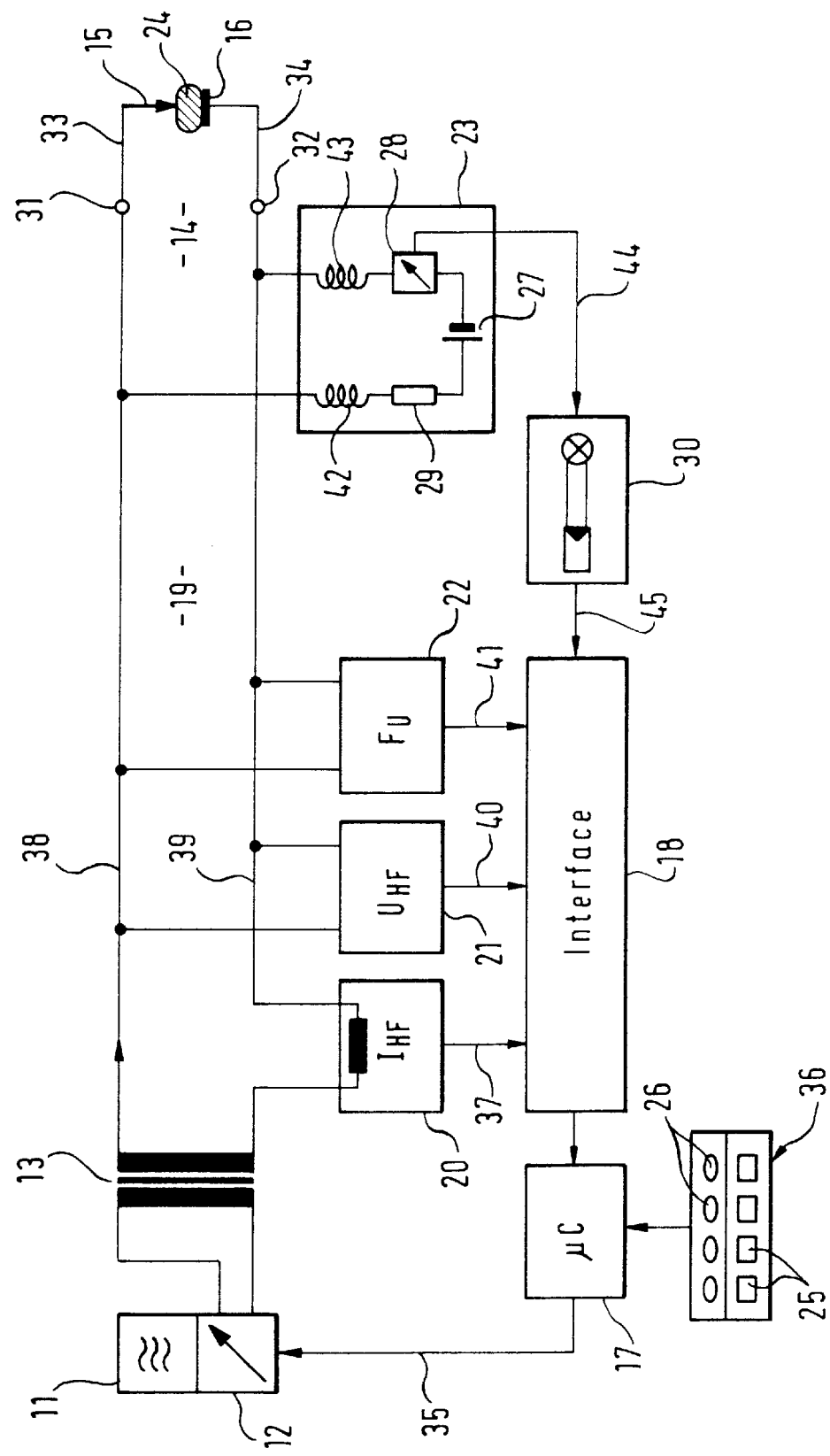

ELECTROSURGICAL HIGH FREQUENCY GENERATOR

FIELD OF THE INVENTION

The invention relates to an electrosurgical high frequency or radiotrequency comprising a high frequency oscillator and a regulatable power stage connected to the latter, with a patient current circuit with an active electrode and a neutral electrode being connectable to the power stage via an output transformer and optionally further galvanic separating rating elements, wherein at least one parameter sensor is provided at the output circuit and is connected via an interface to a microcomputer which regulates the power stage and detects a parameter characteristic for the treatment of the patient, such as the high frequency voltage and/or the high frequency current and/or the intensity of the arc and produces, via the interface and the microcomputer, a regulating signal for the power stage, such that the parameter or the parameters are kept at specific values or in specific value ranges in accordance with a preset mode of operation.

The use of high frequency energy for cutting and coagulation effects on human and animal bodies requires a power dissipation which is oriented towards the application independently of the instrument that is used and of the transition resistance to the tissue. The electro-surgical action which is obtained ultimately depends on many different parameters such as, for example, the stability of the generator, the output voltage, the output current, the cable length to the instrument, the capacity of the cable, the shape and surface of the instrument, the tissue resistance etc.

DESCRIPTION OF THE PRIOR ART

In order to take account of the different influencing parameters, at least to a certain degree, the transmission function "voltage over impedance" or "current over impedance" was determined in older apparatus by a suitable dimensioning of the output transmitter. Accordingly it was a step forward to keep the output current (DE-OS 31 20 102) or the power constant with the aid of current/voltage sensors (DE-OS 25 04 280, DE-OS 27 10 752). A further improvement of the results was achieved in that an impedance value was calculated from the instantaneous values of the current and voltage and was used for the regulation process (DE-OS 31 20 102). A disadvantage of this is however that, with the customary operating frequency, the high frequency generators (300 kHz to 1 MHz), the lead capacitances of the supply leads have a pronounced effect, so that it is not possible to unambiguously determine in the high-ohmic region how large the tissue impedance actually is.

A further embodiment of a high frequency generator operates with a sensor to recognize the presence of sparks or arcs at the position where a cutting effect is to be achieved (EP-OS 0 219 568). A disadvantage of this arrangement is that the voltage increases very strongly as long as the arc is not triggered. To avoid dangers to the patients and to the operator, voltage limiting devices must therefore prevent the voltage increasing too rapidly independently of the power stage which has to be preset.

Furthermore, it is already known (GB-PS 897 961) to feed a DC current into the high frequency output circuit of a high frequency generator by means of which the resistance between the active electrode and the neutral electrode can be determined and can be used to switch on the high frequency.

Finally, it is already known (DE-OS 11 29 927) to determine the correct contact of a neutral electrode on the patient's body by splitting up the neutral electrode into two mutually insulated regions and by applying a DC voltage to these two electrode regions.

OBJECT OF THE INVENTION

The object of the present invention is to provide a high frequency generator of the initially named kind in which a reliable recognition of the true transition resistance between the active electrode and the tissue is possible, throughout the entire operating time, with a fully automatic regulation in the different operating modes, for example in the cutting mode, being hereby possible, and indeed largely independently of the type of electrode used.

BRIEF DESCRIPTION OF THE INVENTION

In order to satisfy this object, the apparatus of the initially named kind is further characterized in that a tissue impedance sensor is additionally provided which is connected to the microcomputer via the interface.

The tissue impedance sensor of the invention is primarily intended to determine whether an adequate contact of the active and neutral electrode with the tissue is present. To this extent, the tissue impedance sensor can also be termed a tissue contact sensor. The function of the tissue impedance sensor or tissue contact sensor is, however, preferably not restricted to determining whether a tissue contact is prevent or not, but rather extends to determining the degree of the contact, or the level of current conducting ability of the tissue, so that a particularly sensitive regulation is possible in dependence on the instantaneous tissue impedance.

In accordance with the invention a customary high frequency generator, which in particular already has high frequency current, high frequency voltage and arc recognition sensors, is supplemented by a tissue impedance recognition sensor. This additional tissue impedance sensor consists generally of an auxiliary generator which generates a signal with a frequency smaller than the working frequency of the high frequency oscillator. Instead of using a signal of low frequency, one can also use a DC voltage. This low frequency or DC voltage is coupled into the output circuit of the high frequency generator. The attenuation of the low frequency auxiliary signal or DC auxiliary signal is now a measure for the quality of the contact between the active electrode and the tissue, or between the active electrode, the tissue of the patient and the neutral electrode. Since this auxiliary signal is also supplied via the lines which are required for the transmission of the high frequency power, the working/useful frequency of the high frequency oscillator must be blocked off by a suitable filter device. In the simplest case, the signal "tissue contact present/not present" can be derived by means of a threshold value switch. A signal which takes account of the extent of the tissue contact and the size of the tissue impedance is however preferably provided, by means of which the regulation of the remaining parameters can be optimized.

BRIEF DESCRIPTION OF THE DRAWING

FIG. 1 shows a block circuit diagram of a high frequency generator in accordance with the invention.

DESCRIPTION OF A PREFERRED EXEMPLARY EMBODIMENT

In accordance with FIG. 1 a high frequency or radiofrequency generator has a high frequency oscillator 11 and a power stage 12 which is fed from the latter and which is connected via an output transformer or transmitter 13 to a high frequency output circuit 19 having two output terminals 31, 32 for connection to an active electrode 15 and to a neutral electrode 16. The feedlines 33, 34, the active electrode 15 and the neutral electrode 16 connected thereto and the body 24 of the patient to which the active electrode 15 and the neutral electrode 16 are applied together form a patient current circuit 14.

The power stage 12 of the high frequency generator of the invention is controllable by a microcomputer 17 to which it is connected via one or more control lines 35.

The microcomputer 17 receives its input information from a keyboard 36 with function keys 25, 26, and also from an interface 18 which receives input signals from a current sensor 20 connected into the output circuit 19, from a voltage sensor 21 connected to the output circuit 19 and also from an arc sensor 22 which is likewise connected to the output circuit 19.

The high frequency current $I_{HP}$ flowing in the output circuit 19 flows through the current sensor 20 and transmits a corresponding signal to the interface 18 via a connection 37.

The voltage sensor 21 is connected to the two output lines 38, 39 of the output circuit 19 and transmits a signal corresponding to the high frequency output voltage $U_{HP}$ to the interface 18 via a connection 40.

The arc sensor 22 measures a parameter at the output circuit 19 characteristic for the occurrence of sparks or of an arc, for example harmonics or certain DC components, and transmits a signal to the interface 18 via a connection 41 which is a measure for the non-presence, creation or presence of an arc between the active electrode 15 and the tissue of the patient's body 24.

In accordance with the invention a tissue impedance sensor 23 is connected to the output circuit 19 of the radio frequency generator and has a DC auxiliary voltage source 27 which is connected via a current limiting resistor 29, a DC current detector circuit 28 and high frequency filters 42, 43 to the output lines 38, 39 of the output circuit 19. The auxiliary voltage source 27 delivers, in co-operation with the current limiting resistor 29, a DC current into the patient current circuit 14 which should not exceed a value of 10 $\mu$A which is non-harmful for the patient's body 24. A signal representative of the DC current which is flowing through the patient current circuit 14 appears at the output of the DC current detector circuit 28 and is likewise fed, via a connection 44, a galvanic separating stage 30, for example in the form of an opto-coupler, and via a further connection 45, into the interface 18, The operation of the high frequency generator described is as follows:

By pressing certain function selection keys 25, 26 on the keyboard 36 a desired mode of operation of the high frequency generator is selected, for example "normal cutting (non-scab forming)", "cutting with scab formation" or "coagulation".

Thereafter, the neutral electrode 16 is applied or secured to a suitable position of the patient's body 24 and the generator is switched on. A high frequency voltage or a high frequency current is now applied via the output transmitter 13 to the output circuit 19 and to the patient circuit 14 connected across the output terminals 31, 32. At each instance, the actual high frequency current $I_{HP}$ is transmitted to the microcomputer 17 by the current sensor 20, the actual high frequency output voltage $U_{HP}$ is transmitted to the microcomputer 17 via the voltage sensor 21 and a signal $F_U$ which is representative of the degree of arc formation is transmitted to the microcomputer via the arc sensor 22.

In addition, the DC transition resistance between the active electrode 15 and the patient's body 24 and the neutral electrode 16 is communicated to the microcomputer 17 from the tissue impedance sensor 23 and the microcomputer 17 recognizes from this whether or not a contact is already present between the active electrode 15 and the patient's body 24 or between the patient's body 24 and the neutral electrode 16. In corresponding manner, the microcomputer 17 controls the power stage 12 to a value which is not dangerous for the surgeon and for the patient.

During the electro-surgical operation the tissue impedance sensor 23 also respectively indicates the actual DC resistance in the patient current circuit 14 to the microcomputer 17 so that the latter can take account of the DC voltage resistance in the patient current circuit 14 in addition to the high frequency current $I_{HP}$, the high frequency $U_{HP}$ and the arc formation signal $F_U$ during The control of the power stage 12.

Whereas all three sensors 20, 21, 22 are preferably provided in addition to the tissue impedance sensor 23, it is at least necessary for the arc sensor 22 or one of the remaining sensors 20, 21 to be present in addition to the tissue impedance sensors 23.

The auxiliary voltage source 27 is illustrated in the drawing as a DC battery. it can however also be realized as a power supply with rectification or as a low frequency AC voltage source, with it only being necessary to pay attention to a suitable galvanic decoupling between the AC voltage side of the power supply and the output circuit 19.

An ideal high frequency energy supply can be automatically ensured in each case as a result of the circuit of the invention, even with very differently shaped active electrodes 15 which represent the treatment instrument.

What is claimed is:

1. An electrosurgical high frequency generator comprising a high frequency oscillator and a regulatable power stage connected thereto with a patient current circuit with an active electrode and a single neutral electrode being connectable to the power stage via an output transformer and, wherein at least one parameter sensor is provided at an output circuit and is connected via an interface to a microcomputer which regulates the power stage and detects a parameter characteristic for a treatment of a patient, such as at least one of high frequency voltage high-frequency current and intensity of an arc and produces, via the interface and the microcomputer, a regulating signal for the power stage such that the parameter or parameters are kept at specific values or in specific value ranges in accordance with a present mode of operation, wherein a tissue impedance sensor is additionally provided which is connected to the microcomputer via the interface and comprises:

an auxiliary voltage source connected to the output circuit or to the patient current circuit, and having substantially lower frequency than the oscillator frequency; and a detector circuit which recognizes the current transmitted by the auxiliary voltage source and which is connected via the interface to the microcomputer.

2. An electrosurgical high frequency generator in accordance with claim 1, wherein a signal from the tissue impedance sensor is given preference in the microcomputer relative to signals from any remaining parameter sensors in such a way that the latter first become fully active when the signal from the tissue impedance sensor signalizes tissue contact necessary for a problem-free treatment.

3. An electrosurgical high frequency generator in accordance with claim 1, wherein a signal "body contacts present" is generated in a low ohmic region on body contact of the active electrode and a signal "body contact not present" is generated in a high ohmic region, when no body contact with the active electrode is present and, in the latter case, the remaining parameters, such as at least one of the high frequency voltage, high frequency current and the high frequency power are regulated down to a safe level.

4. An electrosurgical high frequency generator in accordance with claim 1, wherein the tissue impedance sensor delivers an analog or digital signal to the microcomputer representative of a degree of tissue contact and a current conducting ability a patient's tissue, and wherein regulation of the generator is varied in the microcomputer as a result of signals from any remaining parameter sensors by a signal from the tissue impedance sensor that at any instant the actual degree of tissue contact or actual current conducting ability of the generator is taken into account by the microcomputer.

5. An electrosurgical high frequency generator in accordance with claim 1, with an operating mode "cutting by means of sparks or arc" wherein the power regulation takes place solely by means of the tissue impedance sensor and of any remaining parameter sensors without a power setting element operable from the outside.

6. An electrosurgical high frequency generator in accordance with claim 1, with an operating mode "coagulation" wherein the tissue impedance sensor is also used to determine an ideal degree of coagulation.

7. An electrosurgical high frequency generator in accordance with claim 1, wherein function selection keys are provided for selection of different operating modes, and wherein, on actuating each function key, an amount of influence to be exerted by the tissue impedance sensor is also selected.

8. An electrosurgical high frequency generator in accordance with claim 1, wherein the tissue impedance sensor delivers a signal proportional to a low frequency or DC transition resistance between the active electrode, the patient's body and the neutral electrode.

9. An electrosurgical high frequency generator in accordance with claim 1, wherein a current limiting arrangement is inserted between the auxiliary voltage source and the output circuit or the patient current circuit and restricts the current transmitted from the auxiliary voltage source to a level of 5 $\mu$A to 10 pA which is non-harming for the patient's body.

10. An electrosurgical high frequency generator in accordance with claim 1, wherein a galvanic separating stage is inserted between the detector circuit and the interface.

11. An electrosurgical high frequency generator in accordance with claim 1, wherein a frequency of the auxiliary voltage source is a low frequency of 10 to 100 Hz.

12. An electrosurgical high frequency generator in accordance with claim 1, wherein the auxiliary voltage source is a DC voltage source.

* * * * *